United States Patent

Ogawa et al.

Patent Number: 6,124,926
Date of Patent: *Sep. 26, 2000

[54] DEFECT DETECTING METHOD AND DEVICE

[75] Inventors: Tomoya Ogawa; Nobuhito Nango, both of Tokyo, Japan

[73] Assignees: Ratoc Systems Engineering Co., LTD; Japan Science and Technology Corporation, both of Japan

[*] Notice: This patent issued on a continued prosecution application filed under 37 CFR 1.53(d), and is subject to the twenty year patent term provisions of 35 U.S.C. 154(a)(2).

[21] Appl. No.: 09/237,329

[22] Filed: Jan. 26, 1999

[30] Foreign Application Priority Data

Jan. 26, 1998 [JP] Japan .................................. 10-012793

[51] Int. Cl.$^7$ .................................................. G01N 21/00
[52] U.S. Cl. .................................. 356/237.4; 356/237.5; 356/239.1; 356/318; 356/417
[58] Field of Search .............................. 356/237.1, 237.2, 356/237.3, 237.4, 237.5, 394, 239.1, 239.3, 317, 318, 417, 416; 250/458.1, 459.1, 445, 446

[56] References Cited

U.S. PATENT DOCUMENTS

| | | | |
|---|---|---|---|
| 4,692,690 | 9/1987 | Hara et al. | 356/394 |
| 5,032,735 | 7/1991 | Kobayashi et al. | 356/394 |
| 5,524,152 | 6/1996 | Bishop et al. | 356/425 |
| 5,894,345 | 4/1999 | Takamoto et al. | 356/237.1 |
| 5,936,726 | 8/1999 | Takeda et al. | 356/237.2 |

*Primary Examiner*—Hoa Q. Pham
*Attorney, Agent, or Firm*—Baker & Daniels

[57] ABSTRACT

A defect detecting method and a defect detecting device are provided. An image is formed by scattered light and emitted light from a specimen when a laser beam enters the specimen, and the image is then divided into a plurality of images of different wavelength bands, so that defects can be detected from the plurality of picked up images. Also, scattered light and emitted light incident upon a single objective lens system are divided into a plurality of different wavelength bands and picked up as a plurality of images. The plurality of images of the plurality of different wavelength bands are then combined and displayed in different colors.

9 Claims, 3 Drawing Sheets

EMBODIMENT OF THE OPTICAL SYSTEM

PRINCIPLES

EMBODIMENT OF THE OPTICAL SYSTEM

EMBODIMENT OF THE DIGITAL PROCESSING DEVICE

DEFECT DETECTING METHOD AND DEVICE

BACKGROUND OF THE INVENTION

1. Field of the Invention

The present invention relates to a defect detecting method of detecting defects in crystals or an amorphous material such as an amorphous semiconductor and optical glass, and also to a defect detecting device used in the method.

2. Description of the Related Art

When a laser beam gathered by a condenser lens is incident into the crystal, defects in crystals are detected by an image formed from scattered light and emitted light caused by defects in the crystals of a specimen. The scattered light and emitted light are gathered and focused by an optical system. The light signals transmitted from the specimen include various kinds of light having various wavelengths and intensities, such as elastic scattered light, inelastic scattered light, and photoluminescence light, which are caused in interactions between the entering laser beam and impurities and defects in the host crystals.

Conventional crystal defect detecting methods include a method of detecting defects by observing the total intensity of all the light signals transmitted from the specimen, a method of detecting defects by observing Raman scattering light, and a method of detecting defects by observing photoluminescence light. In these conventional methods, since there is only one specific characteristic light for each inherently physical phenomenon, observation of defects in the crystals has been implemented by taking out such characteristic light respectively.

For instance, the light scattering tomography method is used as an essential way of evaluating and controlling quality of silicon wafers, because of its high performance in detecting defects, such as dislocation, deposition, point defects, plane defects, and segregation impurities, in transparent crystals.

By the light scattering tomography method, however, defects smaller than several tens nm in diameter are difficult to detect due to noise, and high density defects which is beyond the resolving power of the detecting optical system are undetectable. Also, types of defect cannot be identified by this method.

There is another method called Raman scattering tomography method in which a Raman spectroscope is incorporated into a detecting device by the light scattering tomography. By this Raman scattering tomography method, information on the chemical composition of crystal defects can be obtained. However, the signal-to-noise ratio is poor due to the low intensities of the light signals obtained. As a result, it is difficult to distinguish defects from the light signals from the base.

With a method using photoluminescence light, there are problems that detectable defects are limited, and that positional resolving power is low.

As can be seen from the above description, by a single method, light signals generated by factors other than the factor that causes the light signals to be detected result in noise and lower the signal-to-noise ratio. Moreover, using only one method is disadvantageous in that no detailed information on the interrelationship between elastic scattered light, inelastic scattered light, and photoluminescence light can be obtained.

SUMMARY OF THE INVENTION

In recent years, as the circuit structure of an electric device has become complicated, there is an increasing demand for perfection of the crystal structure in the vicinity of the surface of a silicon wafer, However, this demand cannot be satisfied by the light scattering tomography method, the Raman scattering tomography method, or the method using photoluminescence light. There has been no detecting method developed to satisfy the demand so far.

In view of this, the defect detecting method of the present invention is aimed at detecting various information contained in light signals from a detected point by only one laser beam while maintaining identity in terms of space and time. It is also aimed at improving sensitivity in detecting defects in the vicinity of the surface of a wafer, identifying types of defect accurately, and obtaining detailed quantitative information on the defects.

Another object of the present invention is to provide a defect detecting device for practicing the above defect detecting method.

To achieve the above objects, scattered light and emitted light from a specimen are divided into a plurality of different wavelength bands, and defects are identified from a plurality of picked-up images of the plurality of different wavelength bands.

Here, the plurality of images of different wavelength bands can be displayed in different colors, or they can be combined and displayed in different colors.

In accordance with another feature of the present invention, scattered light and emitted light from a specimen incident upon a single objective lens system are divided into a plurality of different wavelength bands, forming a plurality of images of the plurality of different wavelength bands, and thus obtained plurality of images are combined and displayed in different colors.

Here, the plurality of images of different wavelength bands can be picked up as a plurality of synchronized images.

In accordance with yet another feature of the present invention, the entering scattered light and emitted light are transformed into parallel flux by a single objective, and a light dividing unit is provided in the path of the parallel flux. Filters for transmitting light of different wavelength bands can be disposed in the passes of the parallel flux divided by the light dividing unit. Here, an image focus adjustment unit for adjusting the relative distances between image pickup devices and an image forming optical system for forming images on the image pickup devices from the parallel flux divided by the light dividing unit.

Also, the present invention can be utilized in detecting defects, such as bacteria and viruses, in a culture solution or other liquid matters.

With the method and device of the present invention, light signals from a specimen are divided into groups of different wavelength bands by irradiating a laser beam, and then displayed by overlapping the divided signals of the different wavelength bands in different colors. Thus, defect detection can be conducted by elastic scattered light of wavelength bands including the wavelength of the laser beam, and such detection can be conducted by inelastic scattered light or photoluminescence light of other wavelength bands. Moreover, since overlapped patterns obtained from the wavelength bands can be observed, it is easy to identify types of defect or to detect and determine the shapes of defects.

For instance, defects are detected from patterns of elastic scattered light at high sensitivity and high positional resolution, and based on the patterns and intensities of Raman scattered and emitted light of different wavelength bands corresponding to the defective positions, information can be obtained as to the types of defect and the conditions of the adjacent crystals.

Even if the intensities of the light signals of the wavelength bands are greatly different, an image obtained from elastic scattered light of an extremely high signal intensity can be compared with an image obtained from inelastic scattered light of a very weak signal intensity as though the two images were of the same intensity. This can be done by properly selecting the sensitivity and amplification of the image pickup elements.

Furthermore, according to the present invention, the detection can be conducted after eliminating light signals having wavelengths outside a target wavelength band. For instance, elastic scattered light of an intensity weaker than that of inelastic scattered light can be detected, and as a result, the detection sensitivity improves. Also, when detecting inelastic scattered light, only inelastic scattered light of a specified wavelength is selected by completely shutting out elastic scattered light from elastic light noise or defects, so that even very weak inelastic scattered light can be detected at an excellent signal-to-noise ratio.

The above and other objects and features of the present invention will become more apparent from the following description taken in conjunction with the accompanying drawings.

DESCRIPTION OF THE PREFERED EMBODIMENTS

FIG. 1 illustrates the principle of the present invention. In a first series, for instance, an image projected by elastic scattered light is picked up as a monochromatic image (a black-and-white image) by an optical signal transmitted through an optical filter which can transmit light of a wavelength band including the wavelength of an irradiation laser beam. In a second series, an image projected by inelastic scattered light and/or photoluminescence light whose wavelength is different from the wavelength of the irradiation laser beam is picked up as a monochromatic image (a black-and-white image) by an optical signal transmitted through an optical filter which cuts off the optical signal of the wavelength band of the first series and transmits light of a wavelength band different from the wavelength band of the first series.

Figure 1A:
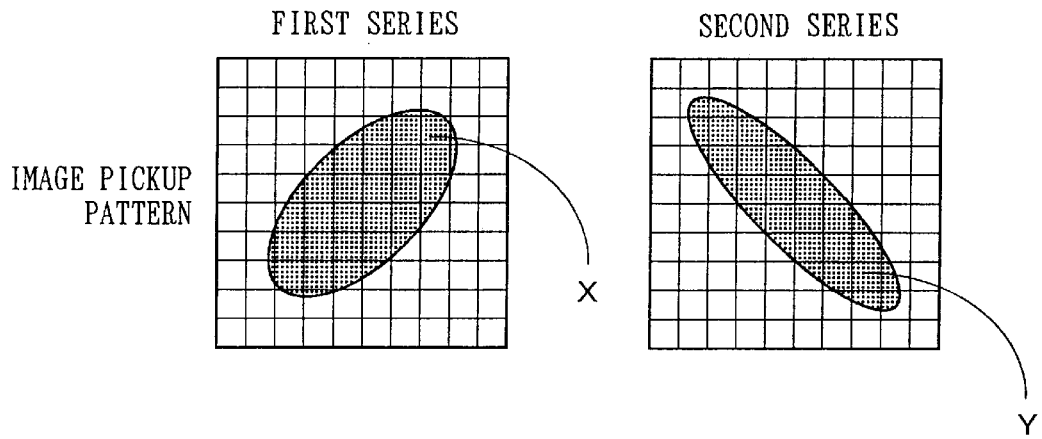
FIGS. 1A to 1C illustrate the principle of the present invention.

FIG. 1A schematically shows a projected pattern on an image pickup device. A pattern of the first series is a wide ellipse X which is inclined upward at the right, while a pattern of the second series is a narrow ellipse Y which is inclined downward at the right. The cells in the drawing represent the existence of picture elements, but the size of each picture element is much smaller than each of the cells.

The patterns on the image pickup elements of the first and second series are read as data of amount of light from picture elements in corresponding positions of the two image pickup devices by synchronizing the two image pickup devices in such a manner as to move rightward from the picture element at the uppermost left, followed by a move rightward from the picture element one below the uppermost left one. Thus, the images of the wavelengths allocated to each series are read as monochromatic analog image signals.

In each series, a color different from the other series is designated to the read image signals. For instance, "red" is designated to the image of the first series, while "blue" is designated to the image of the second series.

Figure 1B:
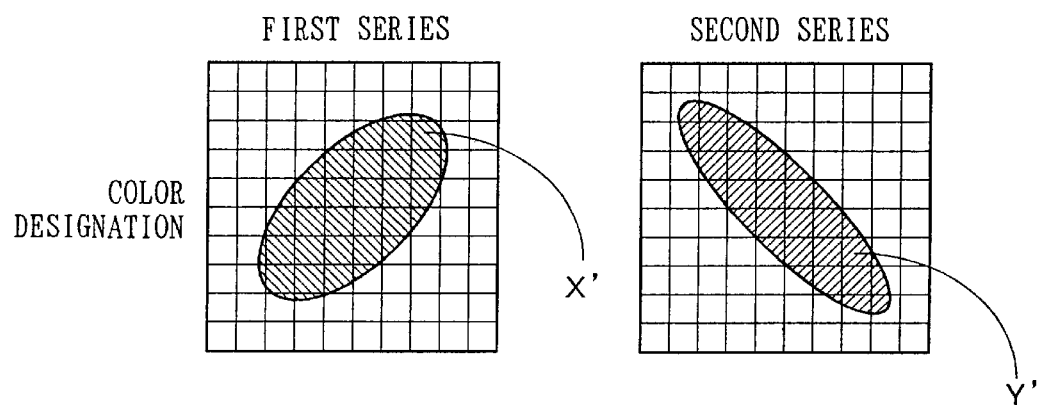

By designating "red" to the image of the first series and "blue" to the image of the second series, the image X' of the first series is displayed in "red" and the image Y' of the second series is displayed in "blue" on a color image display, as shown in FIG. 1B.

Figure 1C:
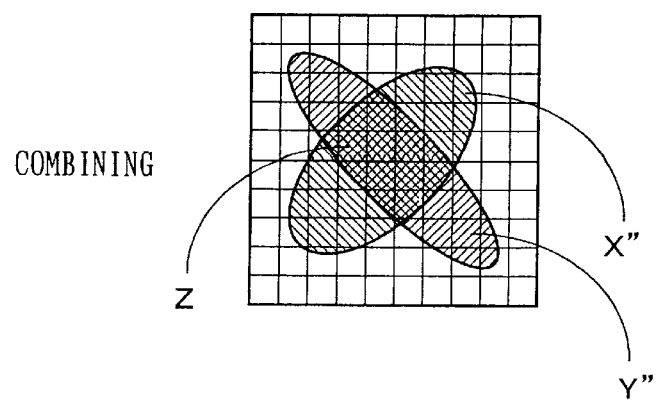

When the images of the first and second series are composed and displayed as one image on the color image display, the elastic scattered light pattern X" of the first series is displayed in red, while the inelastic scattered light and/or photoluminescence light pattern Y" is displayed in blue, as shown in FIG. 1C.

A portion Z where the pattern X" of the first series and the pattern Y" of the second series are overlapped has a composite color of red and blue. If the color image display is a display device which emits color light, such as a cathode-ray tube, the portion Z is displayed in magenta as the composite color of red light and blue light by the additive color process.

Although the above description has been made as to the case where two series are used, more than three series of different wavelengths (for instance, a first wavelength band of the irradiation laser beam, a second wavelength band shorter than the first wavelength band, and a third wavelength band longer than the first wavelength band) can be allocated. In such a case, colors such as "red", "blue", or "green" can be allocated to the display of each series.

By doing so, optical signal patterns formed by elastic scattered light, inelastic scattered light and photoluminescence light can be observed simultaneously. Thus, information on types and shapes of crystal defects can be quickly and accurately obtained.

Figure 2:
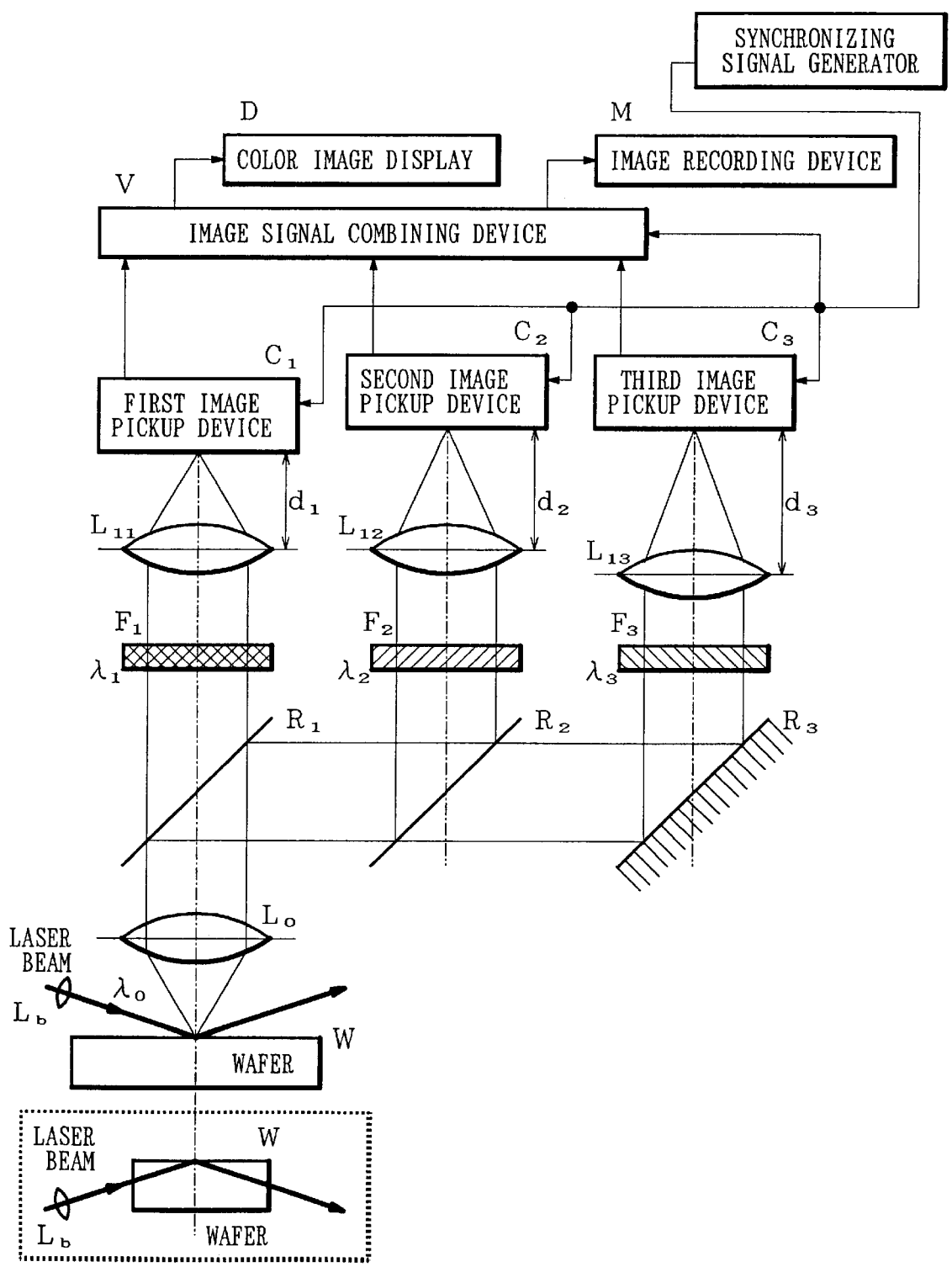
FIG. 2 shows the optical system of one embodiment of the present invention.

FIG. 2 illustrates the optical structure of one embodiment of the present invention, which detects defects in crystals using three series. The first series comprises an objective $L_o$, a semitransparent mirror $R_1$, an optical filter $F_1$, a projection lens $L_{11}$, and an image pickup device $C_1$. The second series comprises an objective $L_o$, a semitransparent mirror $R_1$, a semitransparent mirror $R_2$, an optical filter $F_2$, a projection lens $L_{12}$, and an image pickup device $C_2$. The third series comprises an objective $L_o$, a semitransparent mirror $R_1$, a semitransparent mirror $R_2$, a total reflection mirror $R_3$, an optical filter $F_3$, a projection lens $L_{13}$, and an image pickup device $C_3$.

The semitransparent mirror $R_1$ of the first series and the semitransparent mirror $R_2$ should transmit the light corresponding to a wavelength band $\lambda_1$ and a wavelength band $\lambda_2$ picked up in the series, whether the light is visible light or invisible light such as infrared rays and ultraviolet rays.

An irradiation laser beam is gathered by a condenser lens $L_b$ and irradiated as a dark field illumination on the observation point of a wafer W at the Brewster angle, so that the direct light of the laser beam does not enter the observation .objective. The wafer W then discharges optical signals, including elastic scattered light of the same wavelength as the laser beam, inelastic scattered light of a wavelength different from the incident laser beam, and photoluminescence light, in various directions. Part of the optical signals enters the objective $L_o$.

The same effects can be obtained by concentrating the laser beam from a side of the wafer on the observation point of the wafer at the total reflection angle, instead of irradiating the observation point of the wafer W at the Brewster angle as described above.

It is also possible to conduct a detection on a specimen with right-angle scattered light, inelastic scattered light, or photoluminescence light by irradiating a laser beam from a side of the specimen upon an area in parallel with and in the vicinity of the surface of the specimen.

Since the forward focal point of the objective $L_o$ is situated at the laser beam irradiation point of the wafer, optical signals transmitted from this irradiation point are actually discharged as parallel luminous flux from the objective $L_o$, and reach the semitransparent mirror $R_1$. Part of the optical signals is transmitted through the semitransparent mirror $R_1$, and forms an image on the image pickup device $C_1$ such as CCD via the optical filter $F_1$ and the projection lens $L_{11}$, that transmit optical signals of a wavelength band $\lambda_1$.

Part of the optical signals reflected from the semitransparent mirror $R_1$ moves rightward in the drawing and reaches another semitransparent mirror $R_2$. The part of the optical signals is reflected upward from the semitransparent mirror $R_2$, and then forms an image on the image pickup device $C_2$ having the same photosensitive element arrangement as the image pickup device $C_1$ such as CCD via the optical filter $F_2$ and the projection lens $L_{12}$ that transmit optical signals of a wavelength band $\lambda_2$ longer than the wavelength band $\lambda_1$ transmitted through the optical filter $F_1$. Since the wavelength of the optical signals passing through this route is longer than the wavelength of the optical signals forming an image on the image pickup device $C_1$, the distance $d_2$ between the projection lens $L_{12}$ of the second series and the image pickup device $C_2$ is longer than the distance $d_1$, between the projection lens $L_{11}$, of the first series and the image pickup device $C_1$, if the projection lens $L_{12}$ is the same as the projection lens $L_{11}$, of the first series.

A color selective semitransparent mirror which reflects only light of the wavelength band $\lambda_2$, such as a dichroic mirror, in place of the semitransparent mirror $R_2$, eliminates the need of employing the optical filter $F_2$, and also minimizes damage to the optical signals of the wavelength transmitted through the color selective semitransparent mirror. If the wavelength band reflected from the color selective semitransparent mirror is wider than the desired wavelength band $\lambda_2$, the optical filter $F_2$ can be used together.

By making the focal length of the projection lens $L_{12}$ of the second series adjustable, the distance $d_2$ between the projection lens $L_{12}$ of the second series and the image pickup device $C_2$ can be made equal to the distance $d_1$ between the projection lens $L_{11}$ of the first series and the image pickup device $C_1$.

Further, the part of the optical signals transmitted through the semitransparent mirror $R_2$ moves rightward in the drawing. It is reflected from the total reflection mirror $R_3$ and then forms an image on the image pickup device $C_3$ having the same photosensitive element arrangement as the image pickup device $C_1$ such as CCD via the optical filter $F_3$ and the projection lens $L_{13}$ that transmit optical signals of a wavelength band $\lambda_3$ longer than the wavelength band $\lambda_2$ transmitted through the optical filter $F_2$.

Since the wavelength band of the optical signals forming an image on the image pickup device $C_3$ is longer than the wavelength bands $\lambda_1$ and $\lambda_2$ of the optical signals forming images on the image pickup devices $C_1$ and $C_2$, the distance $d_3$ between the projection lens $L_{13}$ and the image pickup device $C_3$ is longer than the distance $d_1$ between the projection lens $L_{11}$ and the image pickup device $C_1$, and the distance $d_2$ between the projection lens $L_{12}$ and the image pickup device $C_2$.

In order to adjust the distance between each projection lens and each image pickup device depending on the wavelength of a wavelength band, a device may be provided for changing the positions of the image pickup devices without changing the positions of the projection lenses so that the positions of the projection lens $L_{12}$ and the second image pickup device $C_2$ can be easily compared with the positions of the projection lens $L_{11}$ and the second image pickup device $C_1$, and another device may be provided for changing the positions of the projection lenses without changing the positions of the image pickup devices so that the positions of the projection lens $L_{13}$ and the third image pickup device $C_3$ can be easily compared with the projection lens $L_{12}$ and the second image pickup device $C_2$.

Even if the positions of the projection lenses and the image pickup devices are changed as above, images projected on the image pickup devices will not be adversely influenced, because the luminous flux entering a projection lens from an objective via a semitransparent mirror and a total reflection mirror is parallel luminous flux.

The images formed on the image pickup devices $C_1$ to $C_3$ are read as synchronized analog signals by synchronizing signals generated from a synchronizing signal generator S supplied to the image pickup devices $C_1$ to $C_3$. The signals picked up from the image pickup devices $C_1$ to $C_3$ are then transformed into the different color signals by an image signal combining device V. A color image display D displays a light signal of the wavelength band $\lambda_1$ in blue, a light signal of the wavelength band $\lambda_2$ in green, and a light signal of the wavelength band $\lambda_3$ in red. Thus, the relationship between the optical signals of different wavelength bands can be grasped at a glance.

If the wavelength band $\lambda_2$ is made to be a wavelength band including a wavelength $\lambda_0$ of the irradiation laser beam, the elastic scattered light and the inelastic scattered light or photoluminescence light of this wavelength band is displayed in green. An optical signal of the wavelength band $\lambda_1$ is displayed in blue as patterns formed by inelastic scattered light or photoluminescence light of a wavelength shorter than the wavelength band $\lambda_0$ of the irradiation laser beam. An optical signal of the wavelength $\lambda_3$ that is longer than the wavelength $\lambda_0$ of the irradiation laser beam is displayed in red as patterns formed by inelastic scattered light or photoluminescence light of a wavelength longer than the wavelength of the irradiation laser beam.

If the color display is conducted by a color light emitting display device, such as a cathode-ray tube, the area where the blue and the green overlap with each other is displayed in cyan as a combination color by an additive color process of adding the blue light and the green light.

The image signal combining device V is preferably provided with color balancing means for adjusting and selecting colors when displaying the image signals from the image pickup devices $C_1$ to $C_3$ on the color image display D.

An image recording device M is shown in FIG. 2, and this recording device M is a device which can record images displayed on the color image display D described above. For instance, a video tape recorder or a digital video disk device can be used.

Digitized image information leads to a far more effective crystal defect detection device, because it can be processed in various ways, and changed in display colors.

The intensities of optical signals entering each of the image pickup devices greatly vary depending on the spectral distribution of the optical signals based on defects in the detected crystals and the transmittance of the optical filter in the wavelength band. However, it is easy to select and adjust the sensitivity of the image pickup elements, and compensate by changing the amplification of the amplifier.

Figure 3:
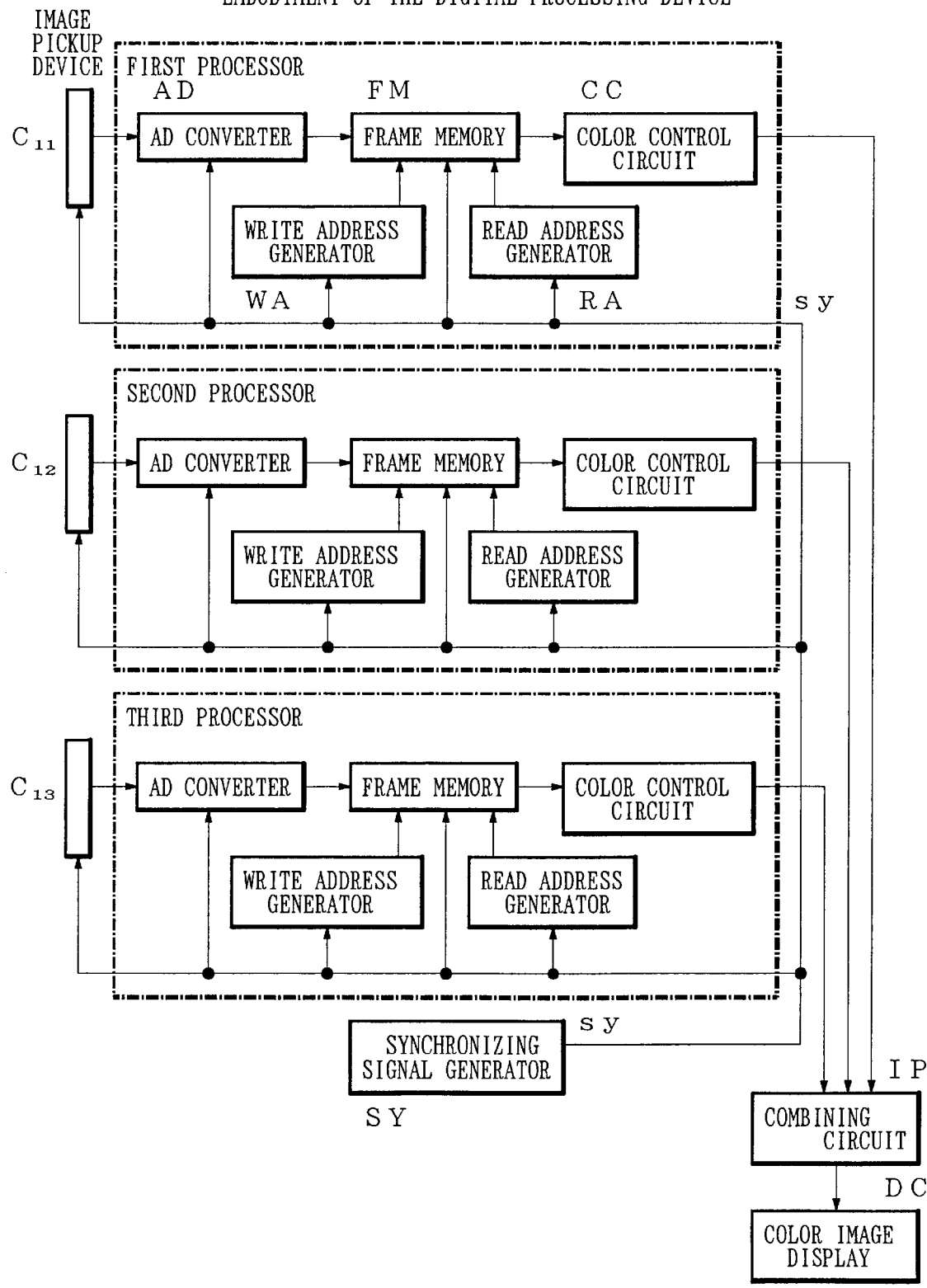
FIG. 3 shows one embodiment of the digital processing device of the present invention.

FIG. 3 shows one embodiment of the digital processing device of the present invention. The digitized data are stored in the frame memory of the digital processing device, which processes image signal output of the image pickup devices $C_{11}$, $C_{12}$, and $C_{13}$ having the same photosensitive element arrangements as the image pickup devices $C_1$, $C_2$, and $C_3$ shown in FIG. 2. The digital processing device of FIG. 3 shows the structures corresponding to the image signal combining device V, the image recording device M, and the color image display D of FIG. 2.

Since the image pickup devices $C_{11}$, $C_{12}$, and $C_{13}$ correspond to the image pickup devices of the first, second and third series, the same optical system as shown in FIGS. 1 and 2 can be employed for projecting optical signals from the wafer onto the image pickup devices $C_{11}$, $C_{12}$, and $C_{13}$.

The analog image signal output from the image pickup devices $C_{11}$, $C_{12}$, and $C_{13}$ are processed by a first processor, a second processor, and a third processor, respectively.

The processors have the same structure, and each of them comprises an AD converter AD, a frame memory FM, a write address generator WA for supplying a write address for the frame memory, a read address generator RA for supplying a read address from the frame memory, and a color control circuit CC for controlling colors for displaying an image sent from the corresponding image pickup device.

If necessary, an amplifier for amplifying the analog image signal output from each image pickup device C can be provided between the image pickup device C and the AD converter AD. The gain of the amplifier is preferably made adjustable so as to adjust the sensitivity of each series or between the series.

The AD converter AD, the frame memory FM, the write address generator WA, and the read address generator RA of each processor are synchronized with the counterparts of the other processors by a synchronizing signal sy transmitted from a synchronizing signal generator SY.

As shown in FIGS. 1 and 2, irradiation of laser beam onto the detection points on the wafer projects the images of the respective wavelength bands on the image pickup devices $C_{11}$, $C_{12}$, and $C_{13}$. The analog image signals from the image pickup devices $C_{11}$, $C_{12}$, and $C_{13}$ synchronized by the synchronizing signal sy are inputted into the respective AD converters, where the analog image signals are converted into digital signals by the common synchronizing signal sy.

The digital signals are then written into each frame memory FM based on the address from the write address generator WA, which designates the write address in the frame memory by the common synchronizing signal sy. The synchronizing signal sy is also used in performing the writing.

Each of the processors is provided with a frame memory FM in this embodiment, so that if the write addresses generated from the synchronized write address generators WA are set to the same address value, the light amount data on the corresponding picture element of each of the image pickup devices is stored at the same address in each frame memory FM.

When reading image data from each frame memory FM, each processor should generate the same address value from the read address generator RA synchronized with the synchronizing signal sy, so that the data on the corresponding picture element of each image pickup device can be read from the frame memory FM of each processor.

The read data are then subjected to color control and adjustment by the color control circuit CC of each processor, and image data are combined by a combining circuit IP. The image data are thus displayed on the image plane of the color image display DC.

As a result, the patterns picked up by the respective image pickup devices $C_{11}$, $C_{12}$, and $C_{13}$, i.e., the patterns of different wavelength bands, are displayed on the image plane in different colors.

Although each of the processor is provided with a frame memory in this embodiment, one frame memory may be shared by a plurality of processors. In such a case, the addresses generated by the write address generators of the processors are different from each other, so that the frame memory can be shared. When reading from the frame memory, the read address generators of the processors generate read addresses having different values.

In the above embodiment, the picture element arrangements, i.e., the numbers of picture elements, of the image pickup devices $C_{11}$, $C_{12}$, and $C_{13}$ are the same for ease of explanation. However, the number of picture elements of an image pickup device which picks up higher definition images of a wavelength of higher positional resolution may be greater than the number of picture elements of the other image pickup devices.

In such a case, to overlap a plurality of images of different wavelengths transmitted from one detection point, the image signals obtained from the image pickup devices having smaller numbers of picture elements are coordinate-transformed to correspond to the positions of the picture elements obtained from the image pickup device having the larger number of picture elements. It is preferable to obtain image data from the image pickup devices having less picture elements corresponding to the positions of the picture elements obtained from the image pickup device having more picture elements.

Although defects are detected in crystals in the above embodiment, it should be understood that the present invention can be utilized in detecting bacteria or viruses in a culture solution or other liquids.

What is claimed is:

1. A crystal defect detecting method, comprising the steps of:

generating scattered light and emitted photoluminescence light from a specimen to be detected by impinging a single laser beam on the specimen;

dividing the scattered light and emitted photoluminescence light into a plurality of wavelength bands;

picking up a plurality of images of the divided plurality of wavelength bands, and identifying defects from the plurality of picked up images.

2. The crystal defect detecting method according to claim 1, further comprising the step of displaying the plurality of picked up images of said plurality of different wavelength bands in different colors.

3. A crystal defect detecting method comprising the steps of:

generating scattered light and emitted photoluminescence light from a specimen to be detected by impinging a single laser beam on the specimen;

dividing the scattered light and emitted photoluminescence light into a plurality of wavelength bands;

picking up a plurality of images of the divided plurality of wavelength bands, and combining and displaying the plurality of picked up images in different colors.

4. A crystal defect detecting device, comprising:

means for dividing scattered light and emitted photoluminescence light, which are generated from defects in a specimen upon impingement of a single laser beam, incident on a single objective lens system into a plurality of wavelength bands;

means for picking up a plurality of images of the plurality of wavelength bands; and means for combining and displaying the plurality of picked up images in different colors.

5. The crystal defect detecting device according to claim 4, wherein images of scattered light and emitted photoluminescence light being divided into a plurality of different wavelength bands are picked up as a plurality of synchronized images.

6. The crystal defect detecting device according to claim 4, wherein incident scattered light and emitted photoluminescence light are transformed into parallel luminous flux by using a single objective lens system, light dividing means is disposed in a part of the parallel luminous flux, and filters for transmitting respective light of different wavelength bands are disposed in paths of a plurality of parallel luminous flux divided by the light dividing means.

7. The crystal defect detecting device according to claim 6, further comprising:

an image forming optical system for forming images on image pickup devices from the parallel luminous flux divided by the light of dividing means, and image focusing means for adjusting the relative distances between image pickup devices and the image forming optical system for forming images on the image pickup devices from the respective parallel luminous flux divided by the light dividing means.

8. The crystal defect detecting device according to claim 5, wherein incident scattered light and emitted photoluminescence light are transformed into parallel luminous flux by using a single objective lens system, light dividing means is disposed in a path of the parallel luminous flux, and filter for transmitting respective light of different wavelength bands are disposed in paths of a plurality of parallel luminous flux divided by the light dividing means.

9. The crystal defect detecting device according to claim 8, further comprising:

an image forming optical system for forming images on image pickup devices from the parallel luminous flux divided by the light dividing means; and image focusing means for adjusting the relative distances between image pickup devices and the image forming optical system for forming images on the image pickup devices from the respective parallel luminous flux divided by the light dividing means.

* * * * *